United States Patent
Semeria et al.

[11] Patent Number: 5,959,127
[45] Date of Patent: Sep. 28, 1999

[54] CERAMIDES, PROCESS FOR THEIR PREPARATION AND THEIR APPLICATIONS IN COSMETICS AND IN DERMOPHARMACY

[75] Inventors: Didier Semeria, Courtry; Michel Philippe, Anthony; Claude Mahieu, Paris, all of France

[73] Assignee: L'OREAL, Paris, France

[21] Appl. No.: 08/923,533

[22] Filed: Sep. 4, 1997

Related U.S. Application Data

[62] Division of application No. 08/321,678, Oct. 12, 1994, Pat. No. 5,665,778.

[30] Foreign Application Priority Data

Oct. 12, 1993 [FR] France ................... 93 12106

[51] Int. Cl.$^6$ .................................. C07C 231/00
[52] U.S. Cl. .................. 554/69; 554/66; 554/68
[58] Field of Search .................. 584/68, 69, 66

[56] References Cited

FOREIGN PATENT DOCUMENTS

| 0 373 038 | 6/1990 | European Pat. Off. . |
| 0 482 860 | 4/1992 | European Pat. Off. . |
| 0 500 437 | 8/1992 | European Pat. Off. . |
| 500437 | 8/1992 | European Pat. Off. . |
| 93/20038 | 10/1993 | WIPO . |

OTHER PUBLICATIONS

Chemical Abstracts, vol. 115 No. 7, Aug. 19, 1991.
Kojima et al, Composition and Molecular Species of Ceramide and Cerebroside in Scarlet Runner Beans (Phaseolus coccineus L.) and Kidney Beans (Phaseolus vulgaris L.), J. Agric. FOod Chem., 1991, 39, pp. 1709–1714.
Kadowaki et al, "Separation of derivatized glycosphingo–lipids into individual molecular species by high performance liquid chromatography", Journal of Lipid Research, vol. 30, No. 4, pp. 616–627.
Yoshida et al, J. Chem. Soc. Perkin Trans 1, 1992, pp. 343–350.
Yoshida et al, Chemistry and Physics of Lipids, vol. 13, pp. 109–116, 1974.
Chem. abstr., 82:97613, 1975.
Chem. abstr of WO–93/20038 displaying reaction mech., 1993.

*Primary Examiner*—Gary Giest
*Assistant Examiner*—Deborah D. Carr
*Attorney, Agent, or Firm*—Jacobson, Price, Holman & Stern, PLLC

[57] ABSTRACT

The ceramides according to the invention are compounds corresponding to the formula:

$$R_1CHOH-CH-CH_2OH$$
$$|$$
$$NHCOR_2$$

in which: $R_1$ is a $C_{11}$ to $C_{21}$ alkyl or alkenyl radical; $R_2$ is a linear or branched $C_1$ to $C_{29}$ hydroxyalkyl radical or a $C_7$ to $C_{29}$ hydroxyaralkyl radical, these compounds being in the form of a racemic mixture of the erythro and threo diastereoisomers for the aminodiol part $$R_1CHOH-CHCH_2OH,$$
$$|$$
$$NH-$$

in erythro:threo ratios of from 85:15 to 20:80.

Application to cosmetic and dermopharmaceutical compositions.

10 Claims, No Drawings

CERAMIDES, PROCESS FOR THEIR PREPARATION AND THEIR APPLICATIONS IN COSMETICS AND IN DERMOPHARMACY

This is a divisional application of Ser. No. 08/321,678, filed Oct. 12, 1994, now U.S. Pat. No. 5,665,778.

The subject of the present invention is novel ceramides, a process for their preparation and their use, in particular for the treatment and care of skin and hair in cosmetics or in dermopharmacy.

Exposure of the skin to the cold, to the sun or to atmospheres with a low relative humidity, repeated treatments with washing compositions or alternatively contact with organic solvents, are factors which result in a visible drying to varying degrees. The skin appears drier and less supple, and the skin surface appears rougher. Furthermore, the hair, which is subjected too often to certain hair treatments, loses its shiny appearance and may become coarse and brittle.

The Applicant has thus sought compounds which allow these phenomena, reflected in a visible drying, to be prevented or corrected and which restore the suppleness to the skin and the shine and softness to hair.

It has already been proposed to use ceramides in order to solve this problem. Indeed, it is known that these compounds are the major consituents of the inter-corneocytic lipids of the stratum corneum and participate in maintaining the integrity of the cutaneous barrier. According to Downing ("The Journal of Investigative Dermatology", vol. 88, No. 3, p. 25–65, March 1987 supplement), they represent approximately 40% of the total amount of these lipids.

The ceramides used in cosmetics are natural extracts derived in particular from pigskin, ox brain, eggs, blood cells, plants etc. (Patent Applications JA 86/260008 and JA 87/120308). Such ceramides have also been proposed for the protection of hair (EP 0,278,505).

They are mixtures, therefore, with a greater or lesser content of ceramides, the composition of which is difficult to master. In addition, these mixtures are subject to bacterial contamination. Their conservation is very difficult to control. When they are of animal origin, there is the further risk of contamination by the agent responsible for BSE (bovine spongiform encephalopathie).

In order to overcome these problems, synthetic ceramides have been proposed, in particular in French Patent Application No. 2,673,179. More particularly, this application describes synthetic ceramides of formula:

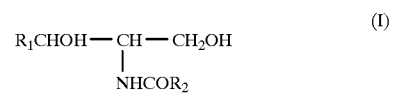

in which R denotes a $C_{11}$ to $C_{21}$ alkyl or alkenyl radical, R' denotes a linear $C_{11}$–$C_{19}$ hydrocarbon radical bearing one or more ethylenic unsaturations or a mixture of linear $C_{11}$–$Cl_9$ hydrocarbon radicals, which may be saturated or bear one or more ethylenic unsaturations, in which the proportion of saturated radicals does not exceed 35%, these compounds being in the form of racemic mixtures of the erythro and threo diastereoisomers in erythro:threo ratios of from 85:15 to 60:40.

These compounds, used in cosmetic or dermopharmaceutical compositions for the treatment and care of the skin and hair, have a moisturizing effect which allows certain visible drying effects on skin or on hair to be prevented or corrected.

However, it would still be desirable to develop compounds which, when used in cosmetic or dermatological compositions, have a greater moisturizing effect than that of the compounds of French Patent Application No. 2,673,179.

Patent Application WO 93/02 656 describes cationic dispersions containing at least one ceramide or glycoceramide or a mixture of natural or synthetic ceramides and/or glycoceramides in which the N-acylating chain is a saturated or unsaturated chain which may contain a hydroxyl group in the alpha position relative to the carbonyl. When they are combined with particular cationic surface-active agents, these aqueous dispersions based on ceramides and/or glycoceramides improve the untangling of hair without making it lank or greasy.

The subject of the present invention is thus novel compounds having an improved power to moisturize skin and/or hair when they are used in cosmetic or dermopharmaceutical compositions.

The novel compounds according to the invention correspond to the formula:

$$R_1CHOH-CH-CH_2OH \atop | \atop NHCOR_2 \qquad (I)$$

in which:
  $R_1$ denotes a $C_{11}$ to $C_{21}$ alkyl or alkenyl radical;
  $R_2$ denotes a linear or branched $C_1$ to $C_{29}$ hydroxyalkyl radical or a $C_7$ to $C_{29}$ hydroxyaralkyl group, the hydroxyl group being in the position alpha to the carbonyl, these compounds being in the form of a racemic mixture of the erythro and threo diastereoisomers for the aminodiol part

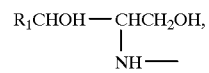

in erythro:threo ratios of from 85:15 to 20:80, preferably from 65:35 to 45:55.

$R_1$ preferably denotes a $C_{13}$ to $C_{19}$ alkyl or alkenyl radical and in particular the pentadecyl radical.

$R_2$ is preferably a linear $C_1$ to $C_{21}$, more particularly a $C_{15}$ to $C_{21}$, 1-hydroxyalkyl radical, in particular the 1-hydroxypentadecyl and 1-hydroxyheneicosyl radicals or a $C_7$ to $C_{19}$ 1-hydroxyaralkyl group, in particular the D, L-1-hydroxybenzyl group.

The compounds of formula (I) according to the invention are waxes which are particularly useful when an effect for combatting the drying of skin or hair is sought in cosmetics or in dermopharmacy.

In particular, the compounds according to the invention display a high activity in the negligible water loss (NWL) test, which is a measurement of the barrier effect, and a good activity in the "Dermodiag" test, which is a test for measurement of the moisturization, whereas analogous compounds which are not present in the form of a racemic mixture of the erythro and threo diastereoisomers display a very low activity in the NWL test and no activity in the "Dermodiag" test, and the compounds, even in the form of a racemic mixture of the erythro and threo diastereoisomers, but not containing an α-hydroxylated N-acylating chain, have no activity in the "Dermodiag" test.

The "Dermodiag" test is a measurement of the conductivity of the skin, which is connected with its degree of moisturization. In this test, a "Dermodiag" apparatus, intended for measuring the degree of moisturization of the upper layers of the epidermis, is used. From the electrical point of view, the skin behaves like a resistor in parallel with a capacitor. These two elements (especially the equivalent capacitor) are very dependent on the water content of the cells.

The apparatus uses the skin as a feedback capacitor and sets into oscillation at variable frequencies depending on the amount of water in the upper tissues. These phenomena take place at high frequency (of the order of several MHz).

The apparatus consists of two concentric electrodes placed on the skin, and the electric field lines are enclosed between these two electrodes. The digital readout on the apparatus then idicates the current consumed at each measurement. The higher the degree of moisturization, the greater is the value displayed.

Furthermore, the compounds display little agressive nature with respect to the skin or the occular mucosae and good tolerance with respect to cell membranes such as those of erythrocytes.

The novel compounds of formula (I) above display emollient and softening properties. They are readily dissolved in the fatty phases of cosmetic or dermopharmaceutical preparations.

Hair treated with these compounds has a shiny appearance and is less water-sensitive, due to the provision of lipid material which is uniformly distributed over the scales of the hair. The mechanical properties and the liveliness are also improved.

In combination with other lipids, these compounds form vesicles.

The ceramides of formula (I) above are obtained by acylation of the amine function of a sphingosine or of a sphinganine or of a reactive derivative of these substances, for example such as the hydrochloride, with a suitable acylating agent.

In the present invention, sphingosine or sphinganine will be understood to refer to the D,L compounds, that is to say the racemic mixtures of the erythro and threo diastereoisomers.

Another subject of the present invention thus relates to a process for the preparation of the compounds of formula (I) which may be represented by the following scheme:

zolides and pyrazolides, and the O-carboxy anhydrides of the suitable corresponding 2-hydroxy acids.

More particularly, the acylating agent is chosen from the O-carboxy anhydrides of the corresponding 2-hydroxy acids and the compounds of formula $R_3COA$ (IV) in which:

$R_3$ is chosen from the radical $R_2$ defined above, linear or branched and $C_7$ to $C_{29}$, preferably $C_7$ to $C_{19}$, aralkyl radicals, substituted in the $\alpha$ position relative to the carbonyl with a substituent chosen from —Br, —CL, —I and —OB, where OB is a group which is capable of forming an —OH group; and A is chosen from halogens,

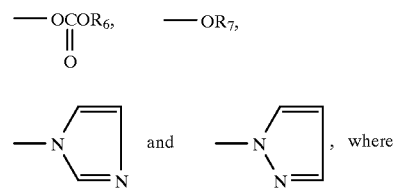

$R_6$ is a $C_2$ to $C_8$ lower alkyl radical and $R_7$ is chosen from $C_1$ to $C_8$ lower alkyl radicals,

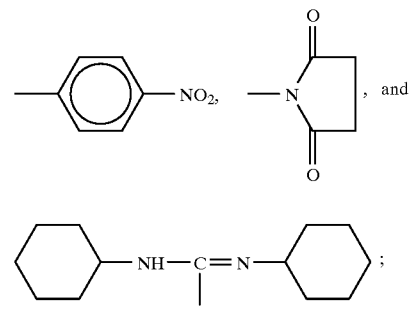

on condition that when $R_3$ represents the radical $R_2$, A is other than —Cl.

Recommended acylating agents are esters of succinimide and of carbodiimide.

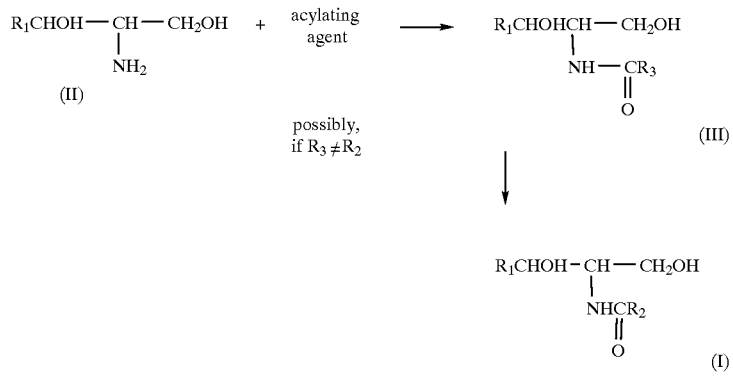

More particularly, the compounds of formula (I) above may be obtained by acylation, in an anhydrous medium or in a suitable solvent, of the amine function of a sphingosine or of a sphinganine of formula (II) above, in which $R_1$ is as defined above, with an acylating agent chosen from acid chlorides, acid anhydrides, mixed anhydrides, para-nitrophenol esters, succinimide esters, carbodiimide esters, $C_1$ to $C_8$ lower alkyl esters, azolides, in particular imida- Depending on the nature of the acylating agent used, the reaction for acylation of the amine group of the compound of formula (II) will be carried out in the anhydrous state or in the presence of a solvent.

Among the solvents which are useful in the process of the present invention there may be mentioned tetrahydrofuran, pyridine, dimethylformamide, dichloromethane and tert-butyl methyl ether.

The group —OB is preferably chosen from the following radicals: acetate, benzoate, benzyloxy, —OSi(CH$_3$)$_3$, —OSi(CH$_3$)$_2$(t-butyl), and —OSi(t-butyl) (C$_6$H$_5$)$_2$.

—OB is preferably an acetate group.

A is preferably chosen from the following radicals:

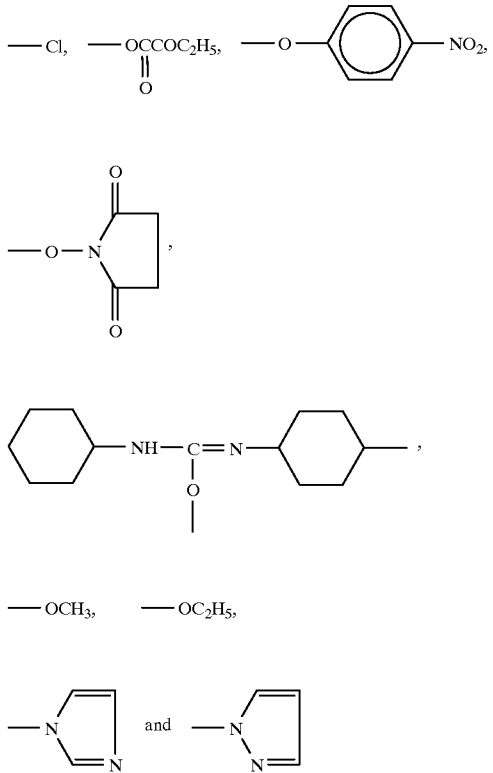

The following radicals are most particularly recommended for A

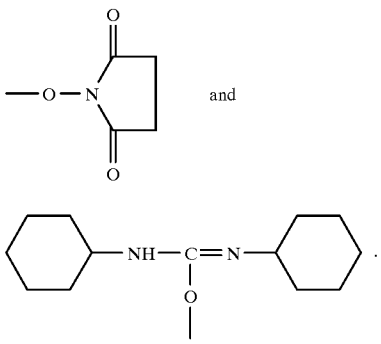

Particularly recommended acylating agents are succinimide 2-hydroxyhexadecanoate, dicyclohexylcarbodiimide 2-hydroxyhexadecanoate, succinimide 2-hydroxydocosanoate, dicyclohexylcarbodiimide 2-hydroxydocosanoate and succinimide D,L-mandelate.

Obviously, when R$_3$ is other than R$_2$ and represents a C$_1$ to C$_{29}$ alkyl or C$_7$ to C$_{29}$ aralkyl radical, which is substituted in the α position relative to the carbonyl as indicated above, one or more additional step(s) is (are) necessary in order to convert the substituent in the α position relative to the carbonyl into a hydroxyl radical in order to obtain the compound of formula (I). This conversion is well known and may, for example, be carried out by hydrolysis.

According to the invention, it is also possible to prepare the compounds of formula (III) for which R$_3$ =R$_2$ by reacting a compound of formula (II) with an O-carboxy anhydride of the corresponding 2-hydroxy acid.

O-Carboxy anhydrides are known compounds which may be obtained by known techniques by reacting the corresponding 2-hydroxy acid with phosgene, or with one of its substituted analogues di- or triphosgene. O-Carboxy anhydrides and processes for their preparation are described in particular by K. Toyooka in Heterocycles vol. 29, No. 5, pages 975–978 (1989).

The acylation reactions with a lower alkyl ester are carried out in the anhydrous state. They are described in particular by E. F. Jordan in JACS p. 600–605 (1961).

The other reactions are carried out in solvents such as, for example, tetrahydrofuran, pyridine, dimethylformamide and dichloromethane.

Acylation with a succinimide ester and a dicyclohexylcarbodiimide ester is described in particular by Lapidot in J. Lipid Res. 8, 142–145 (1967).

Acylation with a para-nitrophenol ester is described in particular by Bodansky in Nature, No. 4459, p. 685 (1955).

Acylation with a mixed anhydride is described by J. L. Torres in Tetrahedron vol 43, No. 17, p. 4031–3 (1987).

The acylations with azolides are described by H. A. Staab in Angew. Chem. Internat. Edit., Vol. 1 No. 7 p. 357–367 (1962).

The acylation reactions are described in general by J. March in Advanced Organic Chemistry—Third Edition— John Wiley & Sons Inc., p. 370–377 (1985).

It is also possible to use the hydrochloride of the compound (II) for the preparation of the compound (I) of the invention.

The compounds (II) are known compounds. Their synthesis has been described in particular by D. Shapiro in "Chemistry of Sphingolipids", Hermann, Paris (1969).

When R$_1$ denotes an alkenyl radical, the compounds (II), in their D,L-erythro forms, are sphingosines, the synthesis of which is described on page 21 of "Chemistry of Sphingolipids".

When R$_1$ denotes an alkyl radical, the compounds (II), in their D,L-erythro forms, are sphinganines, which are also referred to as dihydrosphingosines. They may be prepared in particular from methyl or ethyl 2-acetamido-3-oxoalcanoate as described in "Chemistry of Sphingo lipids", page 32.

The processes for the synthesis of the sphingosines or the sphinganines described above lead to racemic mixtures of the erythro and threo diastereoisomers in erythro/threo ratios of from 85:15 to 20:80.

The compounds of formula (III), and more particularly when R$_3$=R$_2$, derived from the acylation reaction may undergo a reaction for protection of the hydroxyl groups by reaction with a protecting agent chosen from acid anhydrides, acid halides and chlorosilanes, the reaction being followed, after isolation of the product, by a hydrolysis, preferably in a basic medium.

The protecting agents which are useful in the process of the present invention are preferably chosen from acetic anhydride, acetyl chloride, benzoyl chloride, benzyl chloride, benzyl bromide and the chlorosilanes of formula ClSi(CH$_3$)$_3$, ClSi(CH$_3$)$_2$(tBu) and ClSi(tBu) (—C$_6$H$_5$)$_2$.

The compounds according to the invention may be acceptable for various applications, in particular as waxy constituents in cosmetic and dermopharmaceutical compositions. These compounds have, in addition, the property of forming vesicles in combination with other lipids when they are dispersed in water.

The subject of the present invention is thus the use of the lipid compounds of formula (I) as waxy constituents in emulsions, dispersions or in lotions. Its subject is also the use of these compounds, combined with other lipids, for the formation of lipid spherules.

Another subject of the present invention is compositions for cosmetic or dermopharmaceutical use containing a compound of formula (I).

Another subject of the invention consists of a process for the cosmetic treatment of skin, head hair or body hair, consisting in applying to the latter a sufficient amount of such a composition containing a compound of formula (I).

The compositions according to the invention may be provided in the form of emulsions (milk or cream), aqueous-alcoholic, oily or oleo-alcoholic lotions, gels, solid dispersions or solid sticks, sprays or aerosol foams.

According to the invention, the compounds of formula (I) represent 0.05% to 20% and preferably 0.1 to 10% of the total weight of the composition.

The compositions are, for example, emollient lotions, milks or creams, milks or creams for skin or hair care, creams, lotions or milks for removing make-up, foundation bases, sunscreen lotions, milks or creams, artificial tanning lotions, milks or creams, shaving creams or foams, after-shave lotions, shampoos or mascaras.

These compositions may also be provided in the form of lipsticks intended either to colour the lips or to avoid chapping, or make-up products for the eyes or powders and foundations for the face.

When the compositions according to the invention are provided in the form of emulsions of the water-in-oil or oil-in-water type, the fatty phase consists essentially of a mixture of compound of formula (I) with at least one oil, and possibly one other fatty substance.

The fatty phase of the emulsions may constitute from 5 to 60% of the total weight of the emulsion.

The aqueous phase of the said emulsions preferably constitutes from 30 to 85% of the total weight of the emulsion.

The proportion of emulsifying agent may be between 1 and 20% and preferably between 2 and 12% of the total weight of the emulsion.

When the compositions according to the invention are provided in the form of oily, oleo-alcoholic or aqueous-alcoholic lotions, they may constitute, for example, sunscreen lotions containing a screening agent which absorbs UV rays or skin-softening lotions; the oily lotions may additionally constitute foaming oils containing an oil-soluble surfactant, bath oils, etc.

Among the main adjuvants which may be present in the compositions according to the invention there may be mentioned fatty substances such as mineral, animal or vegetable oils or waxes, fatty acids, fatty acid esters such as fatty acid triglycerides having from 6 to 18 carbon atoms, and fatty alcohols; emulsifying agents such as oxyethylenated fatty alcohols or polyglycerol alkyl ethers; solvents such as lower monoalcohols or polyalcohols containing from 1 to 6 carbon atoms, or alternatively water.

The mono- or polyalcohols more particularly preferred are chosen from ethanol, isopropanol, propylene glycol, glycerol and sorbitol.

By way of fatty substance and among the mineral oils there may be mentioned petroleum jelly; among the animal oils there may be mentioned whale, seal, menhaden, halibut liver, cod, tuna, tortoise, ox foot, horse foot, sheep foot, mink, otter, marmot oils etc.; among the vegetable oils there may be mentioned almond, wheat germ, olive, corn germ, jojoba, sesame, sunflower, palm, walnut, karite, shorea, macadamia, blackcurrant seed oils and the like.

Among the fatty acid esters, it is possible to use the saturated or unsaturated $C_{12}$ to $C_{22}$ acid esters of lower alcohols such as isopropanol or glycerol or of saturated or unsaturated, linear or branched $C_8$ to $C_{22}$ fatty alcohols or alternatively of $C_{10}$–$C_{22}$ 1,2-alkane-diols.

There may also be mentioned as fatty substance petroleum jelly, paraffin, lanolin, hydrogenated lanolin, tallow, acetylated lanolin and silicone oils.

Among the waxes there may be mentioned Sipol wax, lanolin wax, beeswax, candelilla wax, microcrystalline wax, carnauba wax, spermaceti, cocoa butter, karite butter, silicone waxes, hydrogenated oils which are solid at 25° C., sucroglycerides, and the oleates, myristates, linoleates and stearates of Ca, Mg and Al.

Among the fatty alcohols there may be mentioned lauryl, cetyl, myristyl, stearyl, palmityl and oleyl alcohol and the alcohols from GUERBET such as 2-octyldodecanol, 2-decyltetradecanol or 2-hexyldecanol.

By way of emulsifying agents and among the polyoxyethyleneated fatty alcohols there may be mentioned lauryl, cetyl, stearyl and oleyl alcohol containing from 2 to 20 moles of ethylene oxide, and among the polyglycerol alkyl ethers there may be mentioned the $C_{12}$–$C_{18}$ alcohols containing from 2 to 10 moles of glycerol.

It may also be useful to employ thickening agents such as cellulose derivatives, polyacrylic acid derivatives, guar gum, carob gum or xanthan gum.

The composition according to the invention may also contain adjuvants commonly used in cosmetics or in dermopharmacy and in particular moisturizing products, softeners, products for treating skin complaints, sunscreen agents, germicides, dyes, preserving agents, perfumes and propellants.

When the compositions according to the invention are dispersions, they may be dispersions of compounds of formula (I) in water in the presence of surfactant or alternatively aqueous dispersions of lipid spherules, consisting of organized molecular layers enclosing an encapsulated aqueous phase, these layers consisting of at least one compound of formula (I) combined with at least one other lipid compound.

To this effect, there may be mentioned as lipid compounds long chain alcohols and diols, sterols such as cholesterol, phospholipids, cholesteryl sulphate and phosphate, long chain amines and their quaternary ammonium derivatives, dihydroxyalkylamines, polyoxyethyleneated fatty amines, long chain amino alcohol esters, their salts and quaternary ammonium derivatives, phosphoric esters of fatty alcohols such as dicetyl hydrogen phosphate or its sodium salt, alkyl sulphates such as sodium cetyl sulphate, fatty acids in the form of salts or alternatively lipids of the type of those described in French Patent Nos. 2,315,991, 1,477,048 and 2,091,516 or in International Patent Applications WO 83/01 571 and WO 92/08685.

It is possible, for example, to use as other lipids, lipids containing a saturated or unsaturated, branched or linear long lipophilic chain containing 12 to 30 carbon atoms, for example an oleyl, lanolyl, tetradecyl, hexadecyl, isostearyl, lauryl or alkylphenyl chain. The hydrophilic group of these lipids may be an ionic or nonionic group. By way of nonionic groups there may be mentioned groups derived from polyethylene glycol. It is also possible to use advantageously, as lipids forming the lamellar phase, polyglycerol ethers such as those described in French Patent Nos. 1,477,048, 2,091,516, 2,465,780 and 2,482,128.

By way of ionic group, a group derived from an amphoteric, anionic or cationic compound may advantageously be used.

Other lipids described in International Patent Application WO 83/01 571 as capable of being used for the formation of vesicles are glycolipids such as lactosylceramide, galactocerebroside, gangliosides and trihexosylceramide, as well as phospholipids such as phosphatidylglycerol and phosphatidylinositol.

Another subject of the present invention is thus a dispersion of lipid spherules consisting of organized molecular layers of compound(s) of formula (I) and of lipid defined above containing an aqueous phase to be encapsulated.

The continuous phase of the dispersion which surrounds the spherules is an aqueous phase.

The spherules in dispersion have a diameter between 0.05 μm and 5 μm.

The encapsulated aqueous phase in the spherules may be water or an aqueous solution of an active substance and is, in this case, preferably iso-osmotic relative to the continuous phase of the dispersion.

The spherules may be obtained in particular according to the process described in French Patent 2,315,991 by the Applicant, according to which a dispersion of spherules is prepared, consisting of organized molecular layers containing an aqueous phase to be encapsulated, by placing together, on the one hand, one or more lipid compound(s) of formula (I) associated with one or more lipid(s) defined above and, on the other hand, the aqueous phase to be encapsulated in the spherules, by stirring in order to ensure mixing and to obtain a lamellar phase, by subsequently adding a dispersion liquid in an amount greater than the amount of lamellar phase obtained and by shaking vigorously for a period ranging from 15 minutes to approximately 3 hours.

The weight ratio between the aqueous phase to be encapsulated and the compound(s) of formula (I) associated with the lipids forming the lamellar phase is preferably between 0.1 and 20.

The weight ratio between the dispersion aqueous phase which is added and the lamellar phase which is dispersed is preferably between 2 and 100, the dispersion phase and the aqueous phase to be encapsulated preferably being iso-osmotic.

The stirring is performed using a shaker stirrer. The process is preferably carried out at a temperature between 30° and 120° C.

Another preparation process may consist in using the process referred to as REV (reverse-phase evaporation vesicle), described in Proc. Natl. Acad. Sci. USA., Vol. 75, No. 9, pages 4194–4198 (1978), by Szoka and Papahadjopoulos.

It is also possible to carry out the process which comprises the sequence of steps consisting in dissolving at least one lipid in at least one water-immiscible organic solvent; in adding the organic phase thus obtained to an aqueous phase; in forming a dispersion of the two phases with vigorous stirring, it being possible for the size of the vesicles to be controlled by varying the stirring speed during this mixing of the phases; in evaporating the solvent(s) with vigorous stirring; and, where appropriate, in concentrating the dispersion.

The active substances may be substances of pharmaceutical or food interest or substances having a cosmetic activity. When they are water-soluble, they are in the aqueous phase encapsulated inside the vesicles.

The water-soluble substances having a cosmetic and/or pharmaceutical activity may be products intended for the care or treatment of skin or hair, for example such as moistening agents such as glycerine, sorbitol, pentaerythritol or pyrrolidonecarboxylic acid and its salts; artificial tanning agents such as dihydroxyacetone, erythrulose, glyceraldehyde or γ-dialdehydes such as tartaric aldehyde, these compounds possibly being associated with dyes; water-soluble sunscreen agents; antiperspirants, deodorants, astringents, freshening, tonic, cicatrizing, keratolytic and depilatory products, or perfumed waters; vegetable tissue extracts such as polysaccharides; water-soluble dyes; anti-dandruff agents; anti-seborrhoeic agents, or oxidizing agents such as bleaching agents, for instance hydrogen peroxide; reducing agents such as thioglycolic acid and its salts.

Vitamins, hormones, enzymes such as superoxide dismutase, vaccines, anti-inflammatory agents such as hydrocortisone, antibiotics, bactericides, cytotoxic agents and anti-tumour agents may also be mentioned.

When the active substances are lipid-soluble, they are found incorporated within the lamellae of the vesicles. They may be chosen from the group formed by lipid-soluble sunscreen agents, substances intended for improving the condition of dry or senile skin, tocopherols, vitamins E, F or A and their esters, retinoic acid, antioxidants, essential fatty acids, glycyrrhetinic acid, keratolytic agents and carotenoids.

A water-immiscible phase L may also be added to the aqueous phase of the dispersions of spherules according to the invention. In particular, the composition according to the invention may contain from 2 to 70% by weight of water-immiscible liquid phase L relative to the total weight of the composition, the relative weight ratio of the constituent lipid(s) of the vesicles with respect to the dispersed liquid phase L being between 0.02/1 and 10/1.

The constituent(s) of the liquid phase L dispersed in the aqueous phase D may be chosen from the group formed by oils such as fatty acid esters of polyols and fatty acid esters of branched alcohols of formula $R^8$—$COOR^9$, in which formula $R^8$ represents a higher fatty acid residue containing from 7 to 19 carbon atoms and $R^9$ represents a branched hydrocarbon chain containing from 3 to 20 carbon atoms; hydrocarbons such as hexadecane, liquid paraffin and perhydrosqualene; halogenated hydrocarbons such as perfluorodecahydronaphthalene; perfluorotributylamine; polysiloxanes; organic acid esters, ethers and polyethers. The liquid phase L may contain at least one perfume and/or at least one lipid-soluble active substance. Such lipid-soluble substances may consist of lipid-soluble sunscreen agents, substances intended for improving the condition of dry or senile skin, tocopherols, vitamins E or F, vitamin A and its esters, retinoic acid, antioxidants, essential fatty acids, glycyrrhetinic acid, keratolytic agents and carotenoids.

It is also possible to add to the dispersions of spherules according to the invention various adjuvants such as opacifying agents, gelling agents, flavours, perfumes or dyes.

The disperions of lipid spherules according to the invention have the advantage of conveying active substances, which are thus masked and protected with respect to the various degrading agents: oxidizing agents and more generally compounds which are reactive towards encapsulated active substances. The penetration and the fixing of the active substances may be modulated by varying the size of the spherules and their electric charge. The action of these active substances may also be delayed in this way (retarding effect). Finally, it is possible, by means of the use of the lipids (I) according to the invention and combined active substances, to obtain a beneficial action which is specific for the active substance used and at the same time a softening action, which is particularly advantageous in the case of treating the skin.

Another subject of the present invention is thus the use in cosmetics of an aqueous dispersion of spherules, consisting of organized molecular layers of lipid compounds (I) associated with other lipids, containing an aqueous phase to be encapsulated, in particular for treating the skin.

Another subject of the invention is the use of such a dispersion of lipid spherules in dermopharmacy or in the food industry.

The present invention will be better illustrated with the following non-limiting examples.

EXAMPLE 1

Preparation of 2-(2'-hydroxyhexadecanoyl) aminooctadecane-1,3-diol

1st Step

Preparation of compound (II) with: $R_1=C_{15}H_{31}$; 2-amino-1,3-octadecanediol hydrochloride (erythro/threo mixture).

Methyl 2-acetamido-3-oxooctadecanoate (100 g, equivalent to 0.27 mol) is suspended in 1 liter of absolute ethanol. The temperature of the reaction medium is brought below 0° C. At this temperature, 30.7 g (0.8 mol) of sodium borohydride are added in three portions and stirring is continued at this temperature for 3 hours. The reaction medium is then brought to reflux of the solvent for 3 hours. After cooling to room temperature, 140 cm³ of concentrated hydrochloric acid are added and the reaction medium is again brought to reflux for 3 hours. This medium is filtered, while still hot, on a sinter funnel. The filtrate is concentrated to dryness under reduced pressure.

The solid obtained is recrystallized from 300 cm³ of 90/10 heptane/ethylacetate solvent mixture. 88 g of a white solid are isolated, for which the acid number measured in ethanol by N/10 sodium hydroxide solution is 2.99 meq/g.

The $^{13}$C NMR spectrum of this solid is in accordance with the expected structure.

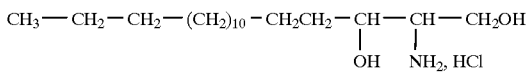

It is sphinganine hydrochloride in D,L erythrothreo racemix mixture form.

2nd Step

Preparation of compound (I) in which —COR$_2$ is a 2-hydroxyhexadecanoyl group.

100 g of 2-hydroxyhexadecanoic acid (D,L mixture) are dissolved in 800 ml of ethyl acetate at 65° C. 41 g of N-hydroxysuccinimide are added and the temperature is allowed to return to about 30° C. 83 g of dicyclohexylcarbodiimide are dissolved in 200 ml of ethyl acetate and this solution is then added to the reaction medium over 20 minutes. The mixture is left stirring for 5 hours at room temperature. The precipitated salts are filtered off on a No. 3 sinter funnel and are rinsed with 100 ml of ethyl acetate at 40° C. The filtrate is evaporated to dryness and the residue is taken up in 200 ml of tetrahydrofuran. This solution, maintained at 60° C., is added over 30 minutes to a solution obtained by dissolving at reflux 108 g of 2-aminooctadecanediol in 800 ml of tetrahydrofuran and 3 ml of triethylamine. The mixture is left stirring for 2 hours at 60° C. 16 ml of water are added and the mixture is left overnight at room temperature. The insoluble material formed is filtered off on a No. 3 sinter funnel and is then washed with 4 times 100 ml of tetrahydrofuran at 40° C.

The combined filtrates are poured into 6 liters of water and 1 ml of concentrated hydrochloric acid with stirring. The precipitate is filtered off on a No. 1 sinter funnel and is then rinsed with 300 ml of acetone. The product is dried in the oven. The derivative is suspended in 700 ml of dichloromethane and then filtered on a No. 3 sinter funnel and dried under vacuum. 130 g (65% crude desired derivative) are thus obtained, which product is resuspended in 350 ml of pyridine. 90 ml of acetic anhydride are added in a single portion. When all the material has dissolved, 60 ml of acetic anhydride are added. The mixture is left stirring for 4 hours at room temperature. The reaction medium is precipitated in a mixture consisting of 2.3 liters of methanol and 1 liter of water, at +4° C., with stirring. The precipitate is filtered off and is then rinsed with 200 ml of water and drained. The precipitate is subsequently taken up in 1 liter of hot heptane and then dried over sodium sulphate and filtered. 130 g of silica are added to the filtrate and the mixture is stirred for 30 minutes. It is filtered and the silica is washed with twice 100 ml of hot heptane. The filtrates are combined and evaporated to dryness. 150 g of the crude peracetylated derivative are thus obtained, which product is subsequently dissolved in 1 liter of methanol with gentle heating. 3.7 g of methanolic 30% sodium methoxide solution are added and the mixture is left stirring for 2 hours. It is neutralized with 24 ml of a mixture of 22 ml of water and 2 ml of concentrated hydrochloric acid. The precipitate formed is filtered off and then dried.

98 g of solid product are obtained, which product is redissolved at 60° C. in 1 liter of ethyl acetate and is recrystallized at +4° C. over 16 hours. After filtration and drying, 93 g (47%) of pure product are obtained.

| ELEMENTAL ANALYSIS | | | | |
|---|---|---|---|---|
| | % C | % H | % N | % O |
| Theoretical | 73.46 | 12.51 | 2.52 | 11.81 |
| Found | 73.56 | 12.55 | 2.53 | 11.68 |

Melting point=89° C.

Erythro/threo ratio of the aminodiol chain: 55/45

$^{13}$C N.M.R. spectrum confirms the expected structure

EXAMPLE 2

Preparation of 2-(2'-hydroxydocosanoyl) aminooctadecane-1,3-diol 50 g of 2-hydroxydocosanoic acid (D/L mixture) are dissolved at 65° C. in 400 ml of tetrahydrofuran. 15.6 g of N-hydroxysuccinimide are added. 31.9 g of dicyclohexylcarbodiimide are dissolved in 100 ml of tetrahydrofuran and, when all the material has dissolved, this solution is added slowly to the reaction medium over 20 minutes.

The mixture is left stirring for 2 h 30. The salts are filtered off on a No. 3 sinter funnel and are rinsed with 50 ml of tetrahydrofuran. This solution, maintained at 60° C., is added over 30 minutes to a solution obtained by dissolving at reflux 41.4 g of 2-aminooctadecane-1,3-diol (obtained in step 1 of Example 1) in 400 ml of tetrahydrofuran and 1.5 ml of triethylamine. The mixture is left stirring at 60° C. for 2 hours. 16 ml of water are added and the mixture is left overnight at room temperature.

The insoluble product formed is filtered off on a No. 3 sinter funnel and is then washed with 100 ml of tetrahydrofuran at 45° C.

The filtrate is poured, over 20 minutes and with stirring, into 3.5 liters of water and 0.5 ml of concentrated hydrochloric acid. The precipitate obtained is filtered off on a No. 1 sinter funnel, drained, rinsed with 300 ml of acetone and then dried. The product obtained is suspended in 200 ml of dichloromethane, filtered off on a No. 3 sinter funnel and drained. 75 g of crude derivative are thus obtained, which product is resuspended in 180 ml of pyridine. 50 ml of acetic anhydride are added in a single portion. When all the material has dissolved, 50 ml of acetic anhydride are added. The mixture is left stirring for four hours at room temperature. The reaction medium is precipitated in a mixture consisting of 2 liters of methanol and 0.5 liter of water, at +4° C., with stirring. The precipitate formed is filtered off and is then rinsed with 200 ml of water and drained. The precipitate is taken up in 600 ml of hot heptane and dried over sodium sulphate and filtered. 80 g of silica are added to the fiiltrate and the mixture is stirred for 45 minutes. It is filtered and the silica is washed with twice 60 ml of dichloromethane. The filtrates are combined and evaporated to dryness. 81 g crude yield of peracetylated derivative are obtained, which product is subsequently dissolved in 55 ml of dichloromethane and 770 ml of methanol. 1.78 g of methanolic 30% sodium methoxide solution are added and the mixture is left stirring for 3 hours. It is neutralized with 12 ml of a mixture consisting of 11 ml of water and 1 ml of concentrated hydrochloric acid. The precipitate formed is filtered off and is then dried. 53 g of solid product are thus obtained, which product is redissolved in 530 ml of ethyl acetate at 60° C. and is recrystallized at +4° C. overnight. After filtration and drying, 48 g (71%) of pure product are obtained.

| ELEMENTAL ANALYSIS | | | | |
|---|---|---|---|---|
| | % C | % H | % N | % O |
| Theoretical | 75.06 | 12.76 | 2.19 | 10 |
| Found | 75.05 | 12.77 | 2.11 | 10.3 |

Melting point=93° C.

Erythro/threo ratio of 2-aminooctadecane-1,3-diol: 54/46

$^{13}$C NMR spectrum confirms the expected structure

EXAMPLE 3

Preparation of 2 -(D,L-mandeloyl) aminooctadecane-1,3-diol 10 g of D,L-mandelic acid are dissolved in 50 ml of tetrahydrofuran, followed by addition of 7.6 g of N-hydroxysuccinimide. 14.95 g of dicyclohexylcarbodiimide are dissolved in 50 ml of tetrahydrofuran and this solution is then added to the reaction medium. The mixture is left stirring for 3 hours at room temperature and the salts formed are then filtered off on a No. 3 sinter funnel and rinsed with 50 ml of tetrahydrofuran.

This solution, maintained at 60° C., is added over 30 minutes to a solution obtained by dissolving at reflux 18.8 g of 2-aminooctadecane-1,3-diol (obtained in step 1 of Example 1) in 100 ml of tetrahydrofuran.

The mixture is left stirring at 60° C. for 3 hours and is then poured into water.

The precipitate formed is filtered off, washed and dried under vaccum at 40° C.

The crude product obtained is recrystallized from 250 ml of methyl acetate.

20 g of pure product are thus obtained (74% yield).

| ELEMENTAL ANALYSIS | | | | |
|---|---|---|---|---|
| | % C | % H | % N | % O |
| Theoretical | 71.68 | 10.41 | 3.22 | 14.69 |
| Found | 71.7 | 10.48 | 3.29 | 14.89 |

Melting point=98–115° C.

$^3$C NMR spectrum confirms the expected structure

Mass spectrum confirms the expected structure

Brythro/threo ratio of the aminodiol chain: 61/39

Example A

Protective Foundation

A foundation having the following composition was prepared:

Aluminium magnesium silicate 0.50 g

Carboxymethyl cellulose sold under the name "BLANOSE 7 LF" by the Company Aqualon 0.15 g Glycerine 3.00 g Preserving agents q.s.

2-(2'-Hydroxyhexadecanoyl)aminooctadecane1,3-diol (compound of Example 1) 1.00 g Lanolin alcohol 1.50 g Glycerol stearate 1.00 g Stearic acid 2.50 g Triethanolamine 1.50 g Capric/caprylic acid triglycerides sold under the name "MIGLYOL 812" n by the Company Hüls 6.00 g Squalane 10.00 g Polyethylene powder 3.00 g Pigments 10.00 g Demineralized water q.s. 100 g The foundation obtained has an improved moisturizing effect.

Example B

Treatment Lipstick

A lipstick having the following composition was prepared:

Liquid lanoline 17.50 g

Microcrystalline wax 15.00 g

Capric/caprylic acid triglycerides sold under the name "MIGLYOL 812" by the Company Hüls 11.00 g Octyl glyceryl behenate 11.0 g 2-(2'-Hydroxyhexadecanoyl)aminooctadecane-1,3-diol (compound of Example 1) 0.20 g Titanium mica 10.00 g Organic pigments 8.00 g Castor oil q.s. 100 g The lipstick obtained has an improved moisturizing effect.

Example C

Mascara Cream

A mascara cream having the following composition was prepared:

Triethanolamine stearate 10.0 g

Candelilla wax 15.0 g

Beeswax 17.0 g

Xanthan gum 1.0 g 2-(2'-Hydroxyhexadecanoyl)aminooctadecane-1,3-diol (compound of Example 1) 0.5 g
Black iron oxide 5.0 g
Aminosilicate polysulphide 4.0 g
Preserving agents q.s.
Water q.s. 100 g The mascara cream obtained has an improved moisturizing effect.

Example D
Protective Hand Cream

A protective hand cream having the following compositions was prepared:
Polyoxyethylenated sorbitan stearate containing 20 mol of ethylene oxide sold under the name "TWEEN 60" by the Company ICI 2.0 g
Cetyl alcohol 1.0 g
Silicone oil of viscosity 200 centistokes ($2.10^{-4}$ m$^2$/s) 7.0 g
Propylene glycol 2.0 g
Crosslinked polyacrylic acid sold under the name "CARBOPOL 940" by the Company Goodrich 0.3 g
Methyl para-hydroxybenzoate 0.3 g
2-(2'-Hydroxyhexadecanoyl)aminooctadecane-1,3-diol (compound of Example 1) 0.5 g
Demineralized water q.s. 100 g The protective cream obtained has an improved moisturizing effect.

Example E
Tinted W/O Care Cream

A care cream having the following composition was prepared:
Cetyldimethicone copolyol sold under the name "ABIL EM 90" by the Company Goldschmidt 5.0 g
Stearalkonium hectorite 2.0 g
Octyldodecanol 8.0 g
Decamethylcyclopentasiloxane 20.0 g
Perfume q.s.
Preserving agent q.s.
Glycerine 3.0 g
Silicone-coated titanium oxide sold under the name "Cosmetic White SIC" by the Company Miyoshi Kasei 4.9 g
Silicone-coated black iron oxide sold under the name "Cosmetic Black SIC" by the Company Miyoshi Kasei 0.7 g
Silicone-coated yellow iron oxide sold under the name "Cosmetic Yellow SIC" by the Company Miyoshi Kasei 0.7 g
Silicone-coated red iron oxide sold under the name "Cosmetic russet SIC" by the Company Miyoshi Kasei 0.7 g
Compound of Example 2 0.50 g
Sodium chloride 1.50 g
Demineralized water q.s. 100 g The cream obtained has an improved moisturizing effect.

Example F
Protective Day Cream

A protective day cream having the following composition was prepared:
Auto-emulsifiable glycerol stearate sold under the name "ARLACEL 165" by the Company ICI 3.0 g
Cetyl alcohol 0.5 g
Stearyl alcohol 0.5 g
Squalane 15.0 g
Sesame oil 10.0 g
Stearic acid 3.0 g
2-Hydroxy-4-methoxybenzophenone sold under the name "UVINUL M40" by the Company BASF 1.0 g
Glycerine 5.0 g
Methyl para-hydroxybenzoate 0.3 g
Compound of Example 2 0.3 g
Demineralized water q.s. 100 g The cream obtained has an improved moisturizing effect.

Example G
Mascara

A mascara having the following composition was prepared:
Triethanolamine stearate 15.0 g
Paraffin 3.0 g
Beeswax 8.0 g
Compound of Example 2 0.5 g
Colophane 2.0 g
Ozokerite 10.0 g
Preserving agents q.s.
Gum arabic 0.5 g
Keratin hydrolysate sold under the name "KERAZOL" by the Company Croda 1.0 g
Pigments 6.0 g
Demineralized water q.s. 100 g The mascara obtained has an improved moisturizing effect.

Example H
Treatment Base for Nails

A treatment base for nails having the following composition was prepared:
Nitrocellulose 12.0 g
Toluenesulphonamide-formaldehyde resin 9.0 g
Camphor 1.0 g
Dibutyl phthalate 6.05 g
Butyl acetate 24.0 g
Ethyl acetate 9.05 g
Isopropyl alcohol 6.0 g
Stearalkonium hectorite 1.0 g
Compound of Example 2 0.01 g
Citric acid 0.02 g
Toluene q.s. 100 g The treatment base obtained has an improved moisturizing effect.

Example I
Lipstick

A lipstick having the following composition was prepared:
Perfume 0.50 g
Caprylic/capric triglycerides sold under the name "MIGLYOL 812" by the Company Hüls 9.10 g
Castor oil 9.10 g
Butylhydroxytoluene 0.16 g
Liquid lanolin 12.80 g
Isopropyl lanolin 4.50 g Compound of Example 2 0.50 g Microcrystalline wax 11.0 g Vinyl acetate/allyl stearate copolymer in a 65/35 ratio 4.50 g Octyl glyceryl behenate 9.10 g Pigments 9.00 g Sesame oil q.s. 100 g The lipstick obtained has an improved moisturizing effect.

Example J

Day Cream for the Face

First Phase

Lipid Phase

Compound of Example 1 1.0 g

Sorbitan palmitate 1.0 g

Cholesterol 0.7 g

Sodium acylglutamate sold under the name "HS 11" by the Company Ajinomoto 0.3 g

α-Tocopherol acetate 0.3 g

Aqueous phase

Glycerine 3.0 g

Preserving agents 0.4 g

Citric acid 0.02 g

Demineralized water q.s. 50 g

Second Phase

Volatile silicone oil 10.0 g

Apricot almond oil 10.0 g

Perfume 0.2 g

Mixture of carboxyvinylic acids sold under the name "CARBOPOL 940" by the Company Goodrich 0.42 g Triethanolamine q.s. pH 6.5

Demineralized water q.s. 100 g

In a first phase, the lipid phase is prepared by mixing, in liquid form, the various amphiphilic lipids of which it is composed and which are associated with α-tocopherol acetate. The lipid phase obtained is placed together with the aqueous phase, so as to obtain a lamellar phase.

The second phase is added to the hydrated lamellar phase obtained. The mixture is subjected to vigorous stirring in a homogenizer, in order to obtain dispersed vesicles in an aqueous dispersion phase.

A white cream of viscosity equal to 15 poises (1.5 Pa/s) is thus obtained. The cream obtained has an improved moisturizing effect.

The compound of Example 1 may be replaced by the compound of Example 2.

We claim:

1. Process for the preparation of a compound of formula:

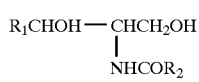
(I)

in which: $R_1$ is a $C_{11}$ to $C_{21}$ alkyl or alkenyl radical; $R_2$ is a linear or branched $C_1$ to $C_{29}$ hydroxyalkyl radical or a $C_7$ to $C_{29}$ hydroxyaralkyl radical, the hydroxyl group being in the position alpha to the carbonyl, the compound being in the form of a racemic mixture of the erythro and threo diastereoisomers for the aminodiol part

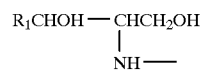

in an erythro/threo ratio of from 85:15 to 20:80 comprising (a) acylating in an anhydrous medium, or in the presence of a suitable solvent, of the amine function of a sphingosine or of a sphinganine of formula:

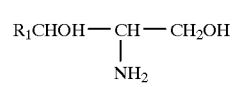
(II)

in which $R_1$ is a $C_{11}$ to $C_{21}$ alkyl or alkenyl radical, this compound being a racemic mixture of the erythro and threo diastereoisomers in an erythro/threo ratio of from 85:15 to 20:80 using an acylating agent selected from the group consisting of acid chlorides, acid anhydrides, mixed anhydrides, para-nitrophenol esters, succinimide esters, carbodiimide esters, $C_1$ to $C_8$ lower alkyl esters, azolides and O-carboxy anhydrides of the corresponding 2-hydroxy acids, in order to obtain a compound of formula:

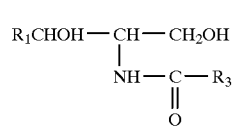
(III)

in which $R_1$ is defined as above and $R_3$ represents either the radical $R_2$ or a radical chosen from linear or branched $C_1$ to $C_{29}$ alkyl radicals or $C_7$ to $C_{29}$ aralkyl radicals which are substituted in the a position relative to the carbonyl, the substituent being selected from the group consisting of radicals —Br, —Cl, —I and —OB, —OB being a group capable of forming an —OH group;

(b) isolating the compound of formula (III); and (c) optionally, when $R_3$ is different from $R_2$, hydrolyzing the compound of formula (III) obtained in order to convert the group —OB into a hydroxyl group.

2. Process according to claim 1, further comprising after the step (a) and before the step (b) protecting the hydroxyl groups by reacting the mixture resulting from step (a) with a protecting agent for —OH groups selected from the group consisting of acid anhydrides, acid halides and chlorosilanes; and, after the step (b) hydrolyzing the compound of formula (III) and recovering the compound of formula (I).

3. Process according to claim 2, wherein the agent for protecting the hydroxyl groups is acetic anhydride, acetyl chloride, benzoyl chloride, benzyl chloride, benzyl bromide or the chlorosilanes of formulae $ClSi(CH_3)_3$, $ClSi(CH)_2(tBu)$ or $ClSi(tBu)(C_6H_5)_2$.

4. Process according to claim 1, wherein the acylating agent corresponds to the formula $R_3COA$ (IV)

in which $R_3$ represents:

either the radical $R_2$ or a radical selected from the group consisting of linear or branched $C_1$ to $C_{29}$ alkyl radicals and $C_7$ to $C_{29}$ aralkyl radicals which are substituted in the α position relative to the carbonyl, the substituent in the α position relative to the carbonyl being selected from the group consisting of the radicals —Br, —Cl, —I and —OB, —OB being a group capable of forming an —OH group; A is selected from the group consisting of halogens,

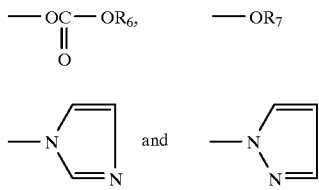

where $R_6$ is a $C_2$ to $C_8$ lower alkyl radical and $R_7$ is selected from the group consisting of $C_1$ to $C_8$ lower alkyl radicals,

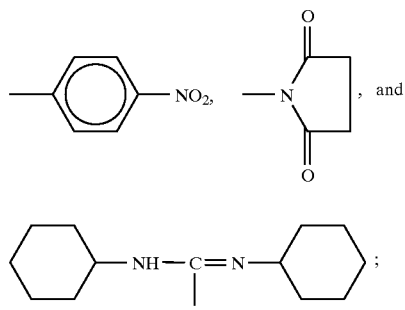

on condition that, when $R_3$ represents the radical $R_2$, A is other than —Cl.

5. Process according to claim 4, wherein the radical —OB of the acylating agent is selected from the group consisting of acetate, benzoate, benzyloxy, —OSi$(CH_3)_3$, —OSi$(CH_3)_2$(tBu) and —OSi(tBu)$(C_6H_5)_2$ groups.

6. Process according to claim 4, wherein the acylating agent is succinimide 2-hydroxydecanoate, dicyclohexylcarbodiimide 2-hydroxyhexadecanoate, succinimide 2-hydroxydocosanoate, dicyclohexylcarbodiimide 2-hydroxydocosanoate or succinimide D,L-mandelate.

7. Process according to claim 6, wherein the compound of formula (II) is 2-aminooctadecane-1,3-diol.

8. Process according to claim 1, wherein $R_1$ is a $C_{13}$ to $C_{19}$ alkyl or alkenyl radical, $R_2$ is a linear or branched $C_1$ to $C_{21}$ hydroxyalkyl radical or a $C_7$ to $C_{19}$ hydroxyaralkyl radical, the erythro/threo ratio of the compound of formula (I) is from 65:35 to 45:55, the erythro/threo ratio of the compound of formula (II) is from 65:35 to 45:55, and $R_3$ is either the radical $R_2$ or a linear or branched $C_1$ to $C_{21}$ alkyl radical or $C_7$ to $C_{19}$ aralkyl radical.

9. Process according to claim 2, wherein the compound of formula (III) is hydrolyzed in a basic medium.

10. Process according to claim 4, wherein $R_3$ is either the radical $R_2$ or a linear or branched $C_1$ to $C_{21}$ alkyl radical or $C_7$ to $C_{19}$ radical.

* * * * *